US011992929B2

(12) United States Patent
Sheffield et al.

(10) Patent No.: US 11,992,929 B2
(45) Date of Patent: May 28, 2024

(54) DEVELOPABLE AND COLLAPSIBLE SHAFT DEPLOYMENT MECHANISM

(71) Applicant: Brigham Young University, Provo, UT (US)

(72) Inventors: Jacob Sheffield, Provo, UT (US); Kendall Hal Seymour, Springville, UT (US); Lance Hyatt, Provo, UT (US); Scott Cunnington, Provo, UT (US); Spencer Magleby, Provo, UT (US); Larry L. Howell, Orem, UT (US); Robert Lang, Alamo, CA (US)

(73) Assignee: Brigham Young University, Provo, UT (US)

( * ) Notice: Subject to any disclaimer, the term of this patent is extended or adjusted under 35 U.S.C. 154(b) by 515 days.

(21) Appl. No.: 17/277,026

(22) PCT Filed: Sep. 18, 2019

(86) PCT No.: PCT/US2019/051728
§ 371 (c)(1),
(2) Date: Mar. 17, 2021

(87) PCT Pub. No.: WO2020/112217
PCT Pub. Date: Jun. 4, 2020

(65) Prior Publication Data
US 2022/0032442 A1 Feb. 3, 2022

Related U.S. Application Data

(60) Provisional application No. 62/732,909, filed on Sep. 18, 2018.

(51) Int. Cl.
*B25G 1/04* (2006.01)
*A61B 17/00* (2006.01)

(52) U.S. Cl.
CPC .......... *B25G 1/04* (2013.01); *A61B 17/00234* (2013.01)

(58) Field of Classification Search
CPC ........................... B25G 1/04; A61B 17/00234
(Continued)

(56) References Cited

U.S. PATENT DOCUMENTS 3,630,105 A 12/1971 Rider
4,327,609 A 5/1982 Resch
(Continued)

FOREIGN PATENT DOCUMENTS

JP 2007511286 A 5/2007
JP 2007532240 A 11/2007
(Continued)

OTHER PUBLICATIONS

Nelson, et al., "Developable Mechanisms on Developable Surfaces," Brigham Young University disclosure 2018-032 (2018).
(Continued)

*Primary Examiner* — Hadi Shakeri
(74) *Attorney, Agent, or Firm* — Dorsey & Whitney LLP

(57) ABSTRACT

A hollow rod developable actuator tool including a first link comprising an outer cylinder, a deployment ring including second link comprising a first portion pivotably connected to the first link at a first joint mounted in a first cavity in the wall of the outer cylinder and a third link comprising a second tool portion pivotably connected to the first portion at a second link, and a fourth link comprising an inner cylinder to which the second portion of the deployment ring is also pivotably connected at a third link mounted in a second cavity in the wall of the inner cylinder. When the inner cylinder of the fourth link is rotated in relation to the outer cylinder of the first link the actuator tool transitions from a first state where the deployment ring is stowed within
(Continued)

the tool to a second state where the deployment ring is deployed externally.

15 Claims, 10 Drawing Sheets

(58) Field of Classification Search
USPC .......................................................... 81/489
See application file for complete search history.

(56) References Cited

U.S. PATENT DOCUMENTS

| | | | |
|---|---|---|---|
| 5,010,797 A | 4/1991 | Stepan | |
| 5,509,923 A | 4/1996 | Middleman et al. | |
| 6,215,081 B1 | 4/2001 | Jensen et al. | |
| 7,409,895 B1 * | 8/2008 | Herrick | B25B 7/02 81/387 |
| 7,540,215 B2 * | 6/2009 | Hoberman | E04B 1/3441 446/487 |
| 9,157,497 B1 | 10/2015 | Magleby et al. | |
| 2005/0251167 A1 | 11/2005 | Voegele et al. | |
| 2008/0234725 A1 | 9/2008 | Griffiths et al. | |
| 2009/0018565 A1 | 1/2009 | To et al. | |
| 2010/0173563 A1 | 7/2010 | Su | |
| 2013/0084180 A1 | 4/2013 | Conley et al. | |
| 2014/0114138 A1 | 4/2014 | Fedorov et al. | |
| 2016/0051127 A1 | 2/2016 | Yoshimura | |
| 2016/0051274 A1 | 2/2016 | Howell et al. | |
| 2017/0354470 A1 | 12/2017 | Farritor et al. | |
| 2018/0078276 A1 | 3/2018 | Chen et al. | |
| 2018/0177516 A1 | 6/2018 | Vardi et al. | |

FOREIGN PATENT DOCUMENTS

| | | |
|---|---|---|
| JP | 2014110920 A | 6/2014 |
| WO | WO-2020/061181 A1 | 3/2020 |
| WO | WO-2020/061190 A1 | 3/2020 |
| WO | WO-2020/112217 A1 | 6/2020 |

OTHER PUBLICATIONS

International Search Report from International Application No. PCT/US2019/051712, dated Dec. 3, 2019.
International Search Report from International Application No. PCT/US2019/051727, dated Dec. 6, 2019.
International Search Report from International Application No. PCT/US2019/051728, dated May 5, 2020.

* cited by examiner

DEVELOPABLE AND COLLAPSIBLE SHAFT DEPLOYMENT MECHANISM

CROSS-REFERENCE TO RELATED APPLICATION(S)

This application is a national stage filing under 35 U.S.C. 371 of International Application No. PCT/US2019/051728, filed Sep. 18, 2019, which claims priority to, and the benefit of, U.S. Provisional Application 62/732,909, filed Sep. 18, 2018, for all subject matter common to both applications. The entire teachings of the above applications are incorporated herein by reference. International Application No. PCT/US2019/051728 was published under PCT Article 21(2) in English.

STATEMENT REGARDING FEDERALLY SPONSORED RESEARCH OR DEVELOPMENT

This invention was made with government support under NSF Award No. 1663345 awarded by the National Science Foundation. The government has certain rights in the invention.

FIELD OF THE INVENTION

The present invention relates to tools, and more specifically to actuating mechanisms disposed within hollow rods suitable for performing tasks such as deploying objects outside the hollow rod from inside.

BACKGROUND

Generally, in the field of tools having actuating mechanisms disposed within hollow cylindrical shafts, tubes, or rods, conventional tools often allow only one mechanism or a single function to operate at the end of the rod. This is especially the case when the inner cross-sectional areas of the hollow rods are small. Although these exist interchangeable attachments to the end of a cylindrical shaft (e.g., screwdriver with differential bits), this still requires the tool to be retracted from the workspace to manually make the switch. Any additional functions generally require an additional independent tool.

SUMMARY

There is a need for hollow rod developable actuator tools having multiple developable actuating mechanisms disposed within hollow rods having small cross-sectional areas. The present invention is directed toward further solutions to address this need, in addition to having other desirable characteristics. Other desirable characteristics include multi-functionality without the need of device retraction or additional tools to perform a function that requires multiple devices.

In accordance with embodiments of the present invention, a hollow rod developable actuator tool is provided. The tool includes a first link comprising an outer cylinder, a first deployment ring having a second link comprising a first portion of the deployment ring and third link comprising a second portion of the deployment ring, and a fourth link comprising an inner cylinder.

The outer cylinder on the first link includes a first end having a first aperture, a second end having a second aperture, a first wall extending between the first end and second end defining an outer circumference of the hollow rod and a central passage therethrough from the first end to the second end, and a first cavity disposed in the first wall having a first joint mounted therein.

The second link comprising the first portion of the first deployment ring includes a first end pivotably coupled to the first wall of the first link at the first joint, a second end having a second joint, and a body extending between first end and second end.

The third link comprising the second portion of the first deployment ring includes a first end pivotably coupled to the body of the second link at the second joint, a second end pivotably connected to a third joint, and a body extending between the first end and second end.

The inner cylinder of the fourth link is disposed in the central passage of the outer cylinder of the first link and includes a first end having a first aperture, a second end having a second aperture, a second wall extending between the first end and the second end defining an inner circumference of the hollow rod and a central passage therethrough from the first end to the second end, and a second cavity in the second wall having the third joint pivotably coupled to the body of the third link.

When the inner cylinder of the fourth link is rotated in relation to the outer cylinder of the first link in such a way that moves the first joint and third joint away from each other along the perimeter of the tool, the tool transitions from a first state wherein the deployment ring is within the first cavity and the second cavity of the respective first wall and second wall to a second state where the deployment ring extends outside the outer circumference of the tool.

In accordance with aspects of the present invention, a device, such as a camera or light, can be attached to the deployment ring. In some such aspects, a mount is provided for attaching the device to the deployment ring.

In accordance with aspects of the present invention, at least one of the body of the second link and the body of the third link are curved to match the curvature of the first link making the second link and third link flush with the outer circumference when the actuator tool is in the first state.

In accordance with aspects of the present invention, the first cavity and the second cavity are located in proximity to the second aperture of the first link and the fourth aperture of the fourth link.

In accordance with aspects of the present invention, the body of the second link pivots around the first joint in a first plane perpendicular to the central passage and the third link pivots around the third joint in a second plane perpendicular to the central passage and offset from the first plane.

In accordance with aspects of the present invention, the second joint connecting the second link and third link of the deployment ring is a compliant segment.

In accordance with aspects of the present invention, the first joint and third joint are compliant segments.

In accordance with aspects of the present invention, the hollow rod developable actuator tool further includes a second deployment ring. The second deployment ring includes a fifth link comprising a first segment of the second deployment ring and a sixth link comprising a second portion of the second deployment ring.

In accordance with aspects of the present invention, the fifth link includes a first portion of the second deployment ring includes a first end pivotably coupled to the first wall of the first link at a fourth joint in a third cavity in the first link, a second end having a fifth joint, and a body extending between first end and second end.

In accordance with aspects of the present invention, the sixth link includes a second portion of the deployment ring that includes a first end pivotably coupled to the body of the fifth link at the fifth joint, a second end pivotably connected to the second wall of the fourth link at a sixth joint in a fourth cavity in the fourth link, and a body extending between the first end and second end.

When the inner cylinder of the fourth link is rotated in relation to the outer cylinder of the first link in such a way that moves the fourth joint and sixth joint away from each other along the perimeter of the hollow rod, the actuator tool transitions from a first state wherein the second deployment ring is within the first cavity and the second cavity of the respective first wall and second wall to a second state where the second deployment ring extends outside the outer circumference of the hollow rod.

In accordance with aspects of the present invention, a device can be attached to the second deployment ring. In certain such aspects, a mount is provided for attaching the device to the second deployment ring.

In accordance with aspects of the present invention, at least one of the body of the fifth link and the body of the sixth link are curved to match the curvature of the first link making the fifth link and sixth link flush with the outer circumference when the actuator tool is in the first state.

In accordance with aspects of the present invention, the fifth joint connecting the fifth link and sixth link of the second deployment ring is a compliant segment.

In accordance with aspects of the present invention, the fourth joint and sixth joint are compliant segments.

In accordance with embodiments of the present invention, a method of using a hollow rod developable actuator tool is provided. The method includes the steps of providing a hollow rod developable actuator tool, and actuating the tool. The hollow rod developable actuator tool is a tool as described herein and includes a first link comprising an outer cylinder, a deployment ring comprising a second link and third link, and a fourth link comprising an inner cylinder.

Actuating the tool involves rotating the inner cylinder of the fourth link in relation to the outer cylinder of the first link in such a way that moves the first joint and third joint away from each other along the perimeter of the tool to transition the tool from a first state to the second state.

In accordance with certain aspects, the method may further include stowing the deployment ring of the tool. This involves rotating the inner cylinder of the fourth link in relation to the outer cylinder of the first link in such a way that moves the first joint and third joint toward each other along the perimeter of the tool to transition the tool from a second state to the first state.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to a hollow rod multi-functional developable actuator tool. This tool includes a cylindrical tube that conceals curved-link (developable) four-bar mechanisms that can actuate to create a deployment ring adjacent to the tube with a hollow center. When the mechanism is closed, the tube resembles a simple cylindrical tube. When the mechanism is open in a deployed stated, then one or more deployment rings extends out beyond the cylindrical tube and can be used to support any number of actuators or devices, etc., while still leaving the central tube hollow during the entire deployment process.

A multitude of deployment rings may be included along the length of the tube. Single or multiple mechanisms on a cylindrical tube can enable the tube to enter a workspace through a confined entrance, then expand to allow a multitude of tools or other devices to enter the workspace and then be held, pointed, oriented, actuated, utilized, etc., without creating multiple entrances to the workspace or the need for additional independent tools. For example, a minimally invasive surgery tool utilizing this invention may enter through a small incision leading to a bodily cavity, such as an abdomen, deploy two cameras from the cylindrical tube using the invention mechanism (see FIG. 2), and then permit the passage of a third tool, such as a pair of forceps, through the original hollow rod cylindrical tube to perform surgical tasks, while the dual cameras provide stereoscopic (3D) vision in the workspace. Many other non-surgical example applications exist, such as attachments for light, cauterizer, laser, vacuum, water jet, power source, and the like.

Compliant components can be included in the system to make the systems be bistable or multistable. Such segments can also be used to put dual systems in the same plane.

Figure 3:
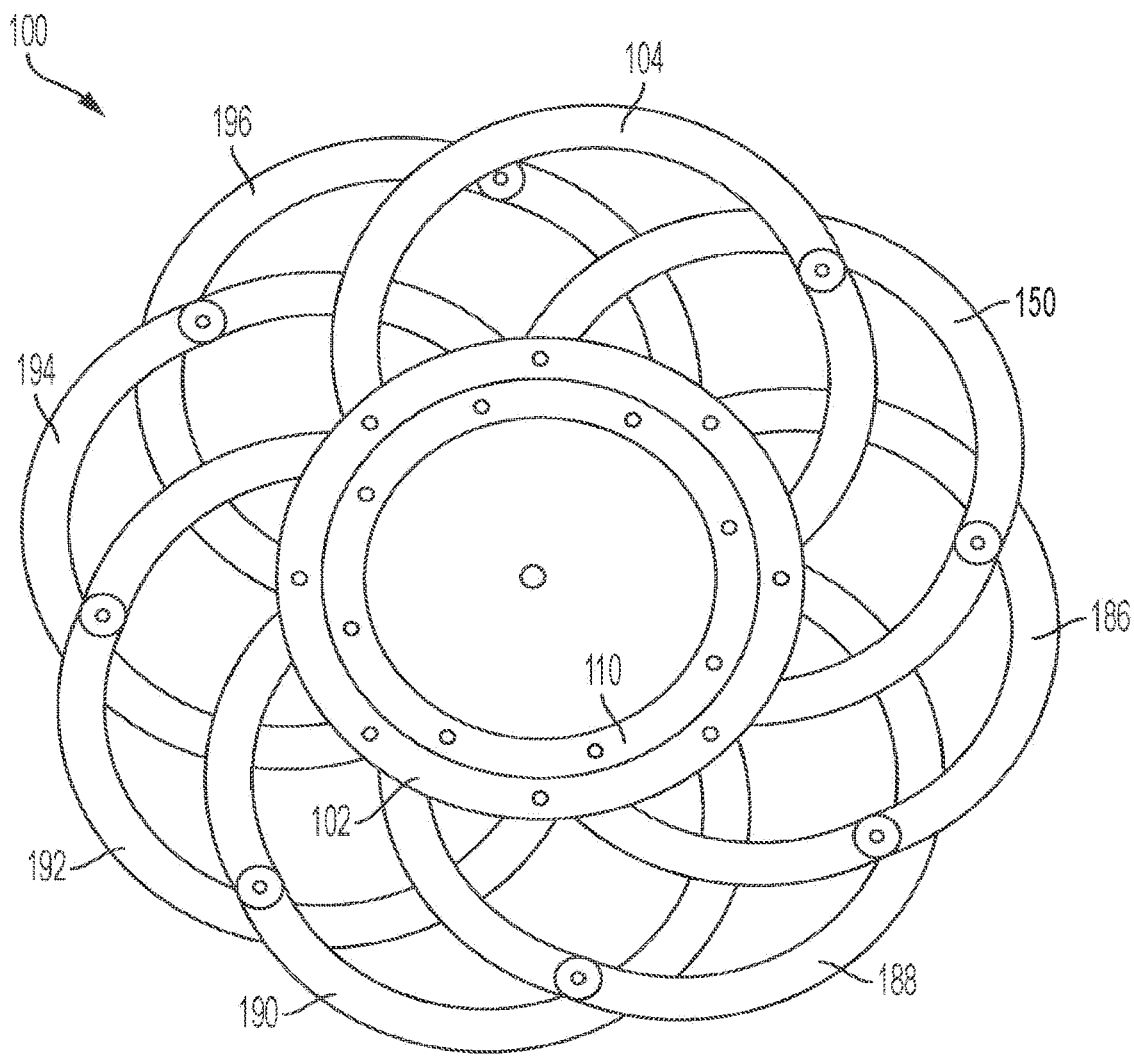
FIG. 3 is a diagrammatic illustration of a hollow rod developable actuator tool having a plurality of deployment rings acting as a dilator.

A plurality of the mechanisms placed on a hollow rod may also enable an expanding/dilating motion, such as a stent or minimally invasive surgical dilation tool (see FIG. 3). This allows for diameter control dilation which is directly proportional to the actuation of the inner cylinder. This provides an advantage over traditional balloon catheters or stents wherein dilation is based on pressure and the actual dilation can vary from patient to patient.

FIGS. 1 through 10, wherein like parts are designated by like reference numerals throughout, illustrate an example embodiment or embodiments of a hollow rod developable actuator tool, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

As utilized herein, the term "developable" has a specific meaning. A developable surface is a shape that can be made from a thin sheet of material without breaking or stretching. The term "developable mechanism" or "developable actuator" are interchangeable terms as utilized herein and describe a mechanism that conforms to or is created from a developable surface. Developable mechanisms can conform to or emerge from developable surfaces such as aircraft fuselages and wings, submarine hulls, rocket cones, and minimally invasive surgery tools. The mechanism is composed of two concentric cylinders.

Also as utilized herein, the inventive mechanism contained within the cylindrical tube or rod is considered "closed" when in an un-deployed first state, nested inside cavities in the tube walls and contained within the outer circumference of the tool, and the inventive mechanism is considered "open" when in a deployed second state, expanding outward from the cavities and beyond the tube walls outside the outer circumference of the tool.

Figure 1:
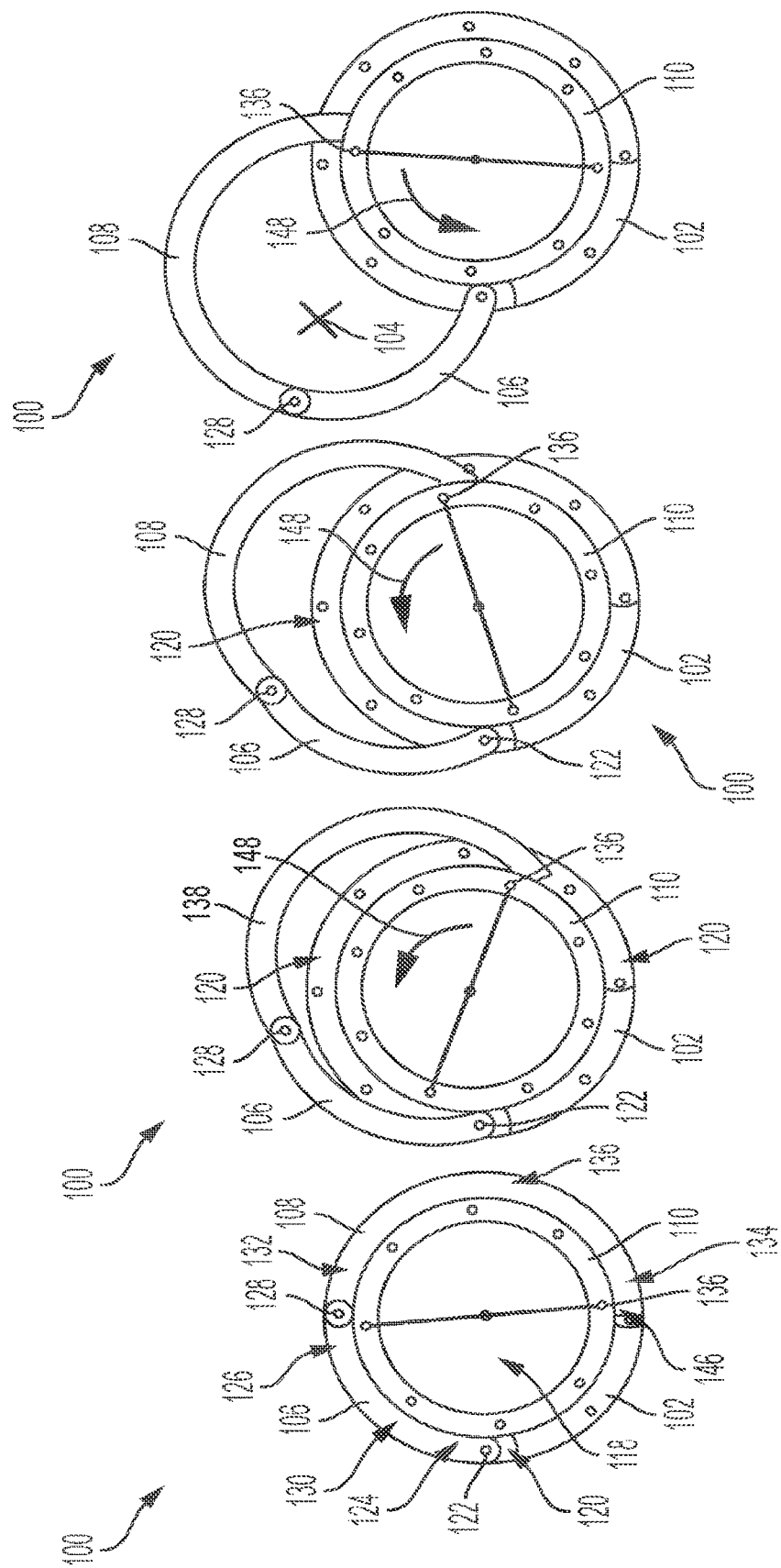
FIG. 1 shows successive illustrations of a hollow rod developable actuator tool with a deployment ring developable actuator mechanism, the tool transitioning through different stages of actuation from stowed within the rod to a deployed ring.
Figure 2:
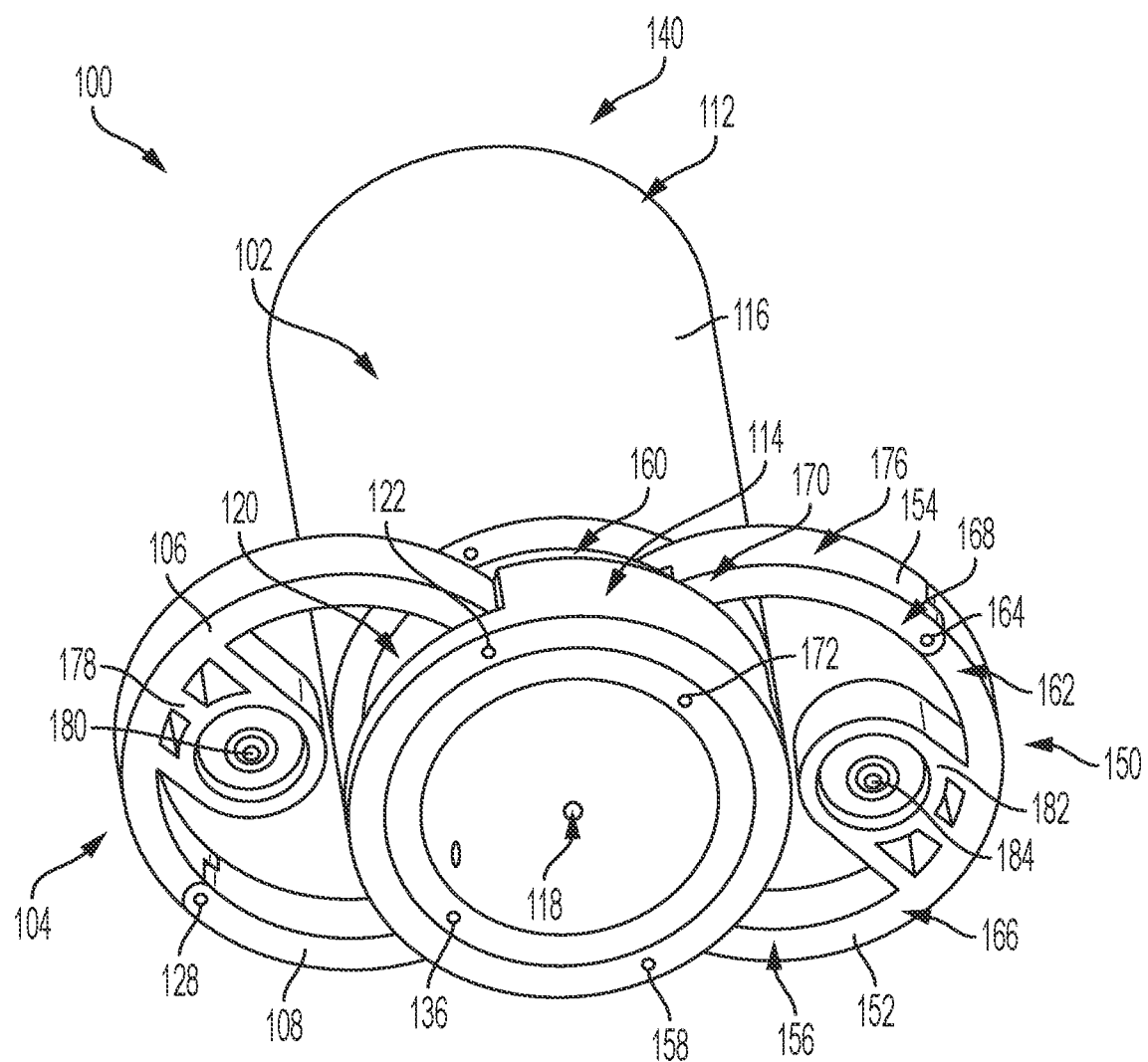
FIG. 2 is an image of the hollow rod developable actuator tool in a deployed, configuration, with devices disposed in the deployment rings.
Figure 4:
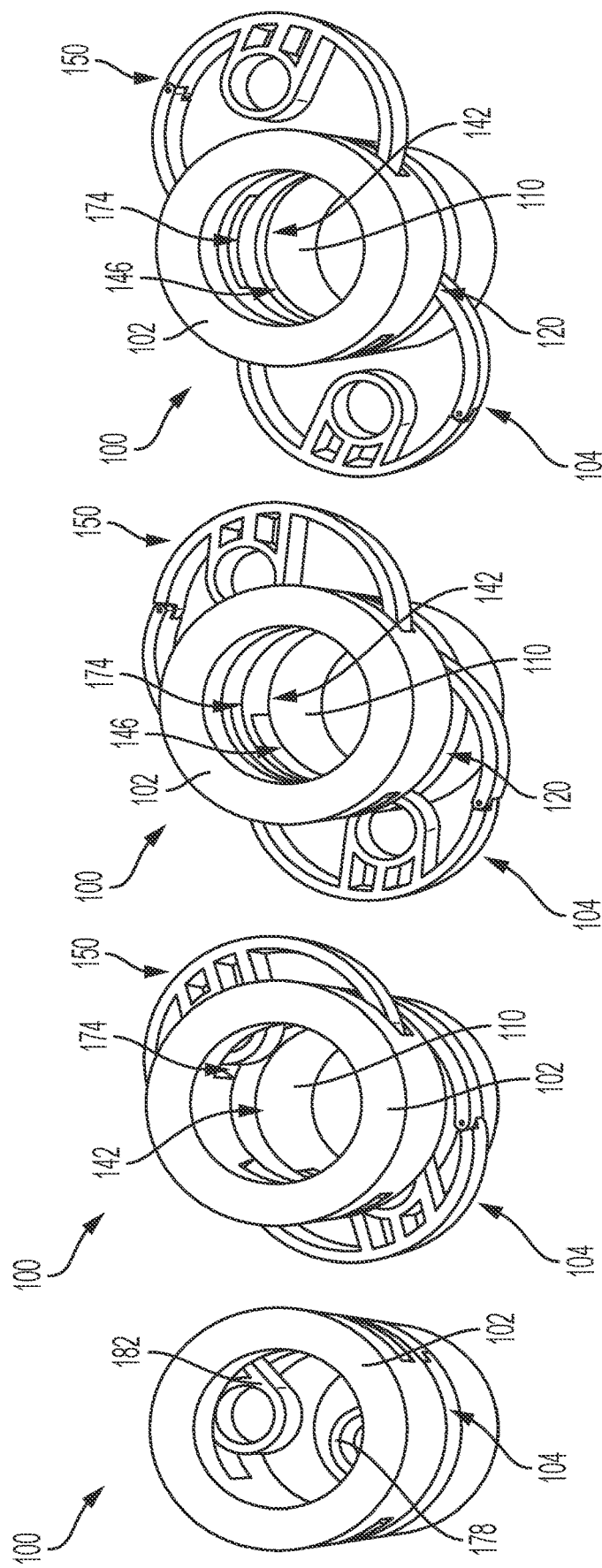
FIG. 4 shows successive illustrations of a hollow rod developable actuator tool with two deployment ring actuator mechanisms, the tool transitioning through different stages of actuation from stowed within the rod, to partially deployed, to fully deployed.
Figure 5:
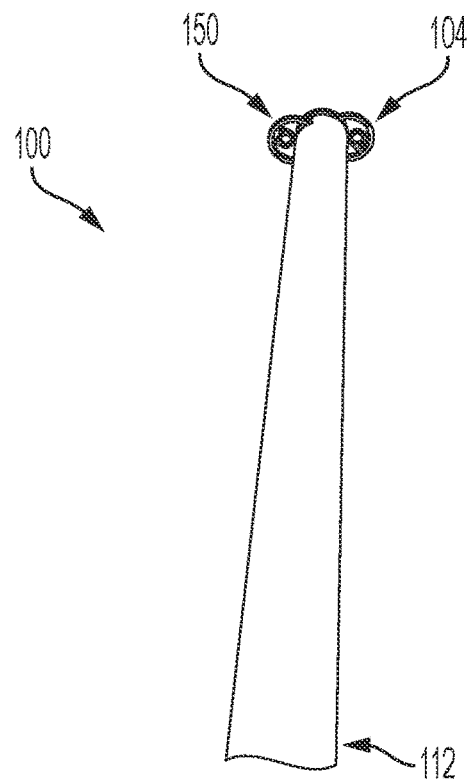
FIG. 5 shows a hollow rod developable actuator tool attached to a longer shaft.

FIG. 1 shows successive top view images of a hollow rod developable actuator tool 100 in operation. FIG. 2 is a perspective view of the hollow rod developable actuator tool 100 with a second deployment ring and mounts attached to the deployment rings. FIG. 3 is a top down view of a hollow rod developable rod actuator having multiple deployment rings. FIG. 4 shows successive images of a hollow rod developable actuator tool 100 in operation. FIG. 5 shows the hollow rod developable actuator tool 100 having an extended shaft.

In the embodiment of FIG. 1, the mechanism of the tool 100 includes two concentric cylinders. A four-bar mechanism, a curved or adapted crank-slider, is fit to the diameter and thickness of the outer cylinder, so that the individual links of the mechanism have the same curvature as the outer cylinder (although this is not a requirement for operation). The elements that make up the four-bar mechanism include a first link 102 comprising the outer cylinder, a first deployment ring 104 comprising a second link 106 and a third link 108, and a fourth link 110 comprising the inner cylinder disposed within the central passage 118 of the first link 102.

The outer cylinder of the first link 102 has a first end 112 having a first aperture, a second end 114 having a second aperture at, and a first wall 116 extending between the first end 112 and second end 114 defining an outer circumference of the hollow rod developable actuator tool 100 and a central passage 118 therethrough from the first end 112 to the second end 114. A first cavity 120 is disposed in the first wall 116 having a first joint 122 mounted therein.

The first wall 116 of the first link 102 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. Other suitable materials will be apparent to one skilled in the art given the benefit of this disclosure. The outer circumference of the first link 102 as well as the length of the first wall 116 between the first end 112 and the second end 114 may vary depending on the intended use or application of the hollow rod developable actuator tool 100.

The first cavity 120 in the first wall 116 comprises an indent, recess, cut-away, channel, passage, window, or the like that is sized and dimensioned to allow the at least a portion of the first deployment ring 104 to reside or otherwise be stowed in the first cavity 120 when the mechanism of the present device is in a closed position. In the certain embodiments the first joint 122 is a pin embedded in the first wall 116 and spanning the first cavity 120. Other suitable joint devices or mechanism will be apparent to one skilled in the art given the benefit of this disclosure.

The second link 106 makes up the first portion of the first deployment ring 104. The second link 106 has a first end 124 pivotably coupled to the first wall 116 of the first link 102 at the first joint 122, a second end 126 having a second joint 128, and a body 130 extending between first end 124 and second end 126. The body 130 of the second link 106 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 130 of the second link 106 is curved to conform to the curvature of the first link 102 such that the body 130 of the second link 106 can reside within the first cavity 120 of the first wall 116 when the tool 100 is in a closed state. In certain embodiments the length of the second link 106 partially determines how far away from the outer cylinder of the first link 102 the first portion of the first deployment ring 104 will travel when actuated. In certain embodiments the second joint 128 is pin embedded in the body 130 at the second end 126 of the second link 106.

The third link 108 makes up the second portion of the first deployment ring 104. The third link 108 has a first end 132 pivotably coupled to the body 130 of the second link 106 at the second joint 128, a second end 134 having a third joint 136, and a body 138 extending between first end 132 and second end 134. The body 138 of the third link 108 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 138 of the third link 108 is curved to conform to the curvature of the first link 102 such that the body 138 of the third link 108 can reside within the first cavity 120 of the first wall 116 when the mechanism is in a closed state. In certain embodiments, the third link 108 can have an arc length of half the circumference of the outer cylinder of the first link 102, which can enable each portion of the first deployment ring 104 to only move outward, or away from, the inner cylinder of the fourth link 110 when actuated, although this is again not a requirement for operation.

The inner cylinder of the fourth link 110 has a first end 140 having a first aperture, a second end 142 having a second aperture, and a second wall 144 extending between the first end 140 and the second end 142 defining an inner circumference of the hollow rod and the central passage 118 therethrough from the first end 140 to the second end 142. A second cavity 146 is disposed in the second wall 144 having the third joint 136 mounted therein and pivotably coupled to the second end 134 of the body 138 of the third link 108.

The second wall 144 of the fourth link 110 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. Other suitable materials will be apparent to one skilled in the art given the benefit of this disclosure. The inner circumference of the fourth link 110 as well as the length of the second wall 144 between the first end 140 and the second end 142 may vary depending on the intended use or application of the hollow rod developable actuator tool 100.

The second cavity 146 in the second wall 144 comprises an indent, recess, cut-away, channel, passage, window, or the like that is sized and dimensioned to allow at least a portion of the first deployment ring 104 to reside or otherwise be stowed in the second cavity 146 when the tool 100 is in a closed position. In certain embodiments, the third joint 136 is a pin embedded in the second wall 144 and spanning the second cavity 146. In such embodiments the second cavity 146 is sized and dimensioned to allow the third link 108 to pivot around the third joint 136. In other embodiments, wherein a first device 180 or mount 178 is attached to the first deployment ring 104, the second cavity 146 is sized and dimensioned to allow the passage of the device or mount through second wall 144 so as to reside in the central passage 118 when the tool 100 is in a closed or stowed state. Other suitable configurations will be apparent to one skilled in the art given the benefit of this disclosure.

The fourth link 110 acts as the slider of the four-bar mechanism (which can be an inner cylinder as shown in the figure or other rotating actuator) which rotates with respect to the outer cylinder of the first link 102 to actuate the mechanism.

The depth (or distance along length of the cylinder) on the first link 102 of the second link 106, third link 108, and fourth link 110 does not change the function of the mechanism, but deeper links may help the extended mechanism resemble an attached cylinder or channel rather than an attached ring or eyelet. Deeper links may also help with additional spring-back forces when creating a bi-stable system. The first link 102 can be a full cylinder, which can extend above and below the rest of the mechanism of the tool 100.

In operation, the inner cylinder of the fourth link 110 is rotated in relation to the outer cylinder of the first link 102 in such a way that moves the first joint 122 and third joint 136 away from each other along the perimeter of the tool, as indicated by arrow 148, the tool 100 transitions from a first state wherein the deployment ring 104 is within the first cavity 120 of the first wall 116, as seen in the left-most image of FIG. 1 to a second state where the second link 106 and third link 108 extends outside the outer circumference of the tool 100 to form the first deployment ring 104 as the seen in the right-most image of FIG. 1.

In certain embodiments, the hollow rod developable actuator tool 100 can include multiple deployment rings. In the embodiment of FIG. 2 the tool 100 has a second deployment ring 150 including as a fifth link 152 comprising a first portion of the second deployment ring 150 and a sixth link 154 comprising a second portion of the second deployment ring 150. The tool 100 of FIG. 2 also includes device mounts 178, 182 securing devices 180, 184 to the deployment rings 104, 150.

The fifth link 152 makes up the first portion of the second deployment ring 150. The fifth link 152 has a first end 156 pivotably coupled to the first wall 116 of the first link 102 at a fourth joint 158 in a third cavity 160, a second end 162 having a fifth joint 164, and a body 166 extending between first end 156 and second end 162. The body 166 of the fifth link 152 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 166 of the fifth link 152 is curved to conform to the curvature of the first link 102 such that the body 166 of the second link 106 can reside within a third cavity 160 of the first wall 116 when the tool 100 is in a closed state. In certain embodiments the length of the fifth link 152 partially determines how far away from the outer cylinder of the first link 102 the first portion of the second deployment ring 150 will travel when actuated. In certain embodiments the fourth joint 158 is pin embedded in the body 166 at the second end 162 of the fifth link 152.

The sixth link 154 makes up the second portion of the second deployment ring 150. The sixth link 154 has a first end 168 pivotably coupled to the body 166 of the fifth link 152 at the fifth joint 164, a second end 170 having a sixth joint 172 in a fourth cavity 174 in the fourth link 110, and a body 176 extending between first end 168 and second end 170. The body 176 of the sixth link 154 may be formed of plastic, metal, or any other material suitable for forming a developable surface. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In certain embodiments, the body 176 of the sixth link 154 is curved to conform to the curvature of the first link 102 such that the body 176 of the sixth link 154 can reside within the third cavity 160 of the first wall 116 when the mechanism is in a closed state. In certain embodiments, the sixth link 154 can have an arc length of half the circumference of the outer cylinder of the first link 102, which can enable each portion of the second deployment ring 150 to only move outward, or away from, the inner cylinder of the fourth link 110 when actuated, although this is again not a requirement for operation.

To accommodate the deployment and storage of the second deployment ring 150, the first link is provided with a third cavity 160 having the fourth joint 158 mounted therein. The third cavity 160 in the first wall 116 comprises an indent, recess, cut-away, channel, passage, window, or the like that is sized and dimensioned to allow the at least a portion of the second deployment ring 150 to reside or otherwise be stowed in the third cavity 160 when the mechanism of the present device is in a closed position. In the certain embodiments the fourth joint 158 is a pin embedded in the first wall 116 and spanning the third cavity 160. In the embodiment of FIG. 2 where the second deployment ring 150 is located adjacent to the first deployment ring 104 along the length of the tool 100, the third cavity 160 extends from the first cavity 120. Other suitable joint devices or mechanism will be apparent to one skilled in the art given the benefit of this disclosure.

Similarly, the fourth link 110 is provided with a fourth cavity 174 having the sixth joint 172 mounted therein. The fourth cavity 174 in the second wall 144 comprises an indent, recess, cut-away, channel, passage, window, or the like that is sized and dimensioned to allow at least a portion of the second deployment ring 150 to reside or otherwise be stowed in the second cavity 146 when the tool 100 is in a closed position. In certain embodiments, the sixth joint 172 is a pin embedded in the second wall 144 and spanning the fourth cavity 174. In such embodiments the fourth cavity 174 is sized and dimensioned to allow the sixth link 154 to pivot around the sixth joint 172. In other embodiments, wherein a first device 180 or mount 178 is attached to the second deployment ring 150, the fourth cavity 174 is sized and dimensioned to allow the passage of the first device 180 or mount 178 through second wall 144 so as to reside in the central passage 118 when the tool 100 is in a closed or stowed state. In the embodiment of FIG. 2 where the second deployment ring 150 is located adjacent to the first deployment ring 104 along the length of the tool 100, the fourth cavity 174 extends from the second cavity 146. Other suitable configurations will be apparent to one skilled in the art given the benefit of this disclosure.

In the embodiment of FIG. 2, the first deployment ring 104 is provided with a first mount 178 on the second link 106 holding a first device 180 while the second deployment ring 150 is provided with a second mount 182 on the fifth link 152 holding a second device 184. The type of device 180, 184 depends on the use the tool 100 is configured for. In this embodiment the first device 180 and second device 184 are cameras. Other suitable devices 180, 184 will be apparent to one skilled in the art given the benefit of this disclosure. In a similar manner, the mounts 178, 182 can be configured as necessary to hold or otherwise interact with any number of devices 180, 184. In certain embodiments, the mounts 178, 182 are formed of the same material as the portion of their respective deployment rings 104, 150. In other embodiments, the mounts 178, 182 are formed of a different material and attached to the respective deployment ring 104, 150.

FIG. 3 depicts a top down view of an embodiment of a hollow rode developable actuation tool 100 having several deployment rings. In this embodiment, the tool 100 further includes a third deployment ring 186, fourth deployment ring 188, fifth deployment ring 190, sixth deployment ring 192, seventh deployment ring 194, and eighth deployment ring 196 in addition the first deployment ring 104 and second deployment ring 150. Each of the deployment rings 186, 188, 190, 192, 194, and 196 have structure like the first and second deployment rings 104, 150 with a first portion pivotably connected to the first link 102 and a second portion pivotably connected to the first portion and the fourth link 110 allowing all of the deployment rings to be actuated by the rotation of the inner cylinder of the fourth link 110 in relation to the outer ring of the first link 102. The plurality of the deployment rings 104, 150, 186, 188, 190, 192, 194, and 196 placed on a tool 100 can enable an expanding/dilating motion, such as a stent or minimally invasive surgical dilation tool.

FIG. 4 shows successive images of a 3D printed implementation of a tool 100 with two deployment rings 104, 150. The left-most image is the tool in a closed or stowed state while the rightmost image is the tool in an open deployed state. In the example of FIG. 4 the inner cylinder of fourth link 110 does not extend the full length of the tool 100. The second end 142 of the fourth wall end where the first deployment ring 104 and second deployment ring 150 are mounted on the length of the tool 100. In this example, the first link 102 extending from the location of the first deployment ring 104 and second deployment ring 150 to the second end 114 defines both the inner and outer circumference of the tool. In this manner the first link 102 serves as a cap enclosing the mechanisms of the tool. Here the second cavity 146 and fourth cavity 174 are formed by the spacing between where the first link 102 sit on top of the fourth link 110 with the first deployment ring 104 and second deployment ring 150 positioned therebetween. The tool 100 of FIG. 4 is actuated by rotating the inner cylinder of the fourth link 110 in relation to outer cylinder of the first link 102 at the first ends 112, 140 of the respective links 102, 110.

FIG. 5 shows an hollow rod developable actuator tool 100 wherein the outer cylinder of the first link 102 and the inner cylinder of the fourth link 110 are extended to form a longer shaft having the first deployment ring 104 and second deployment ring 150 proximate to the distal second ends 114, 142 of the respective links 102, 110. The tool 100 of FIG. 5 is actuated by rotating the inner cylinder of the fourth link 110 in relation to outer cylinder of the first link 102 at the first ends 112, 140 of the respective links 102, 110 proximate to the user.

Figure 6:
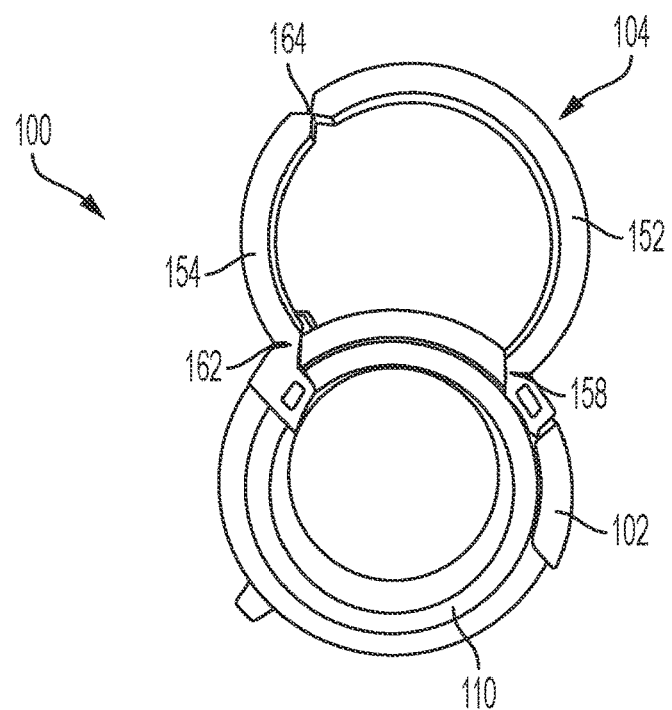
FIG. 6 shows a compliant version of the mechanism illustrated in FIG. 1.
Figure 7A:
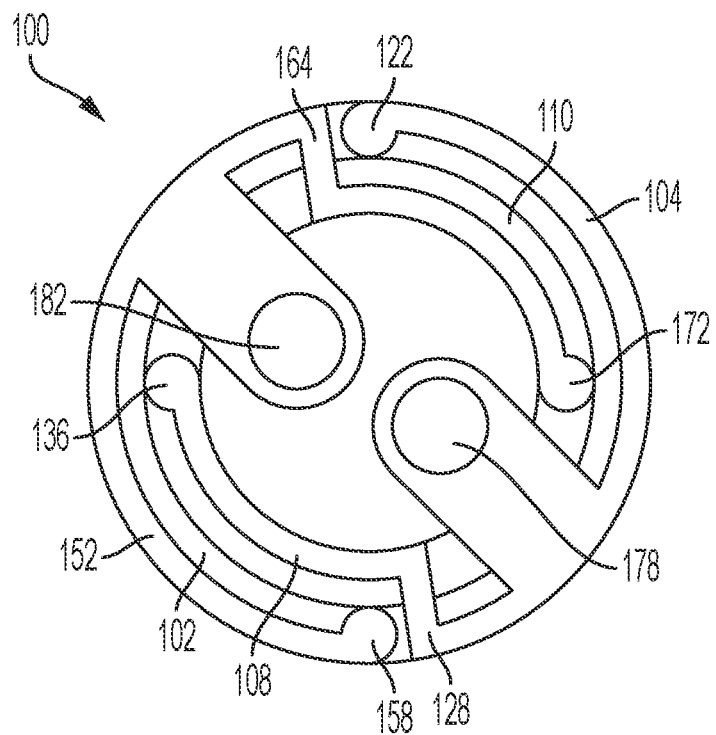
FIGS. 7A and 7B show compliant versions of the mechanism deployment ring in a stowed configuration and then in a fully deployed configuration, notably the deployment rings are in the same plane because of their compliant configuration.
Figure 7B:
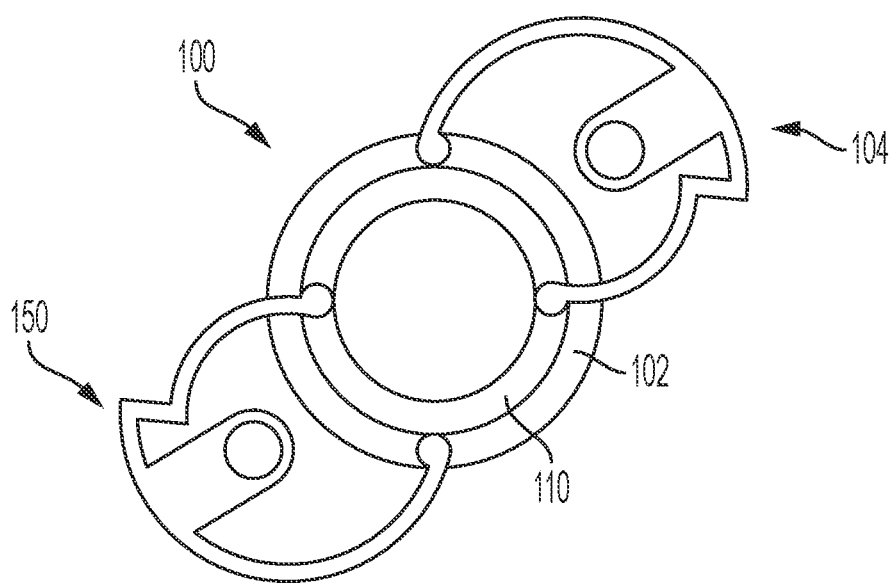
Figure 8A:
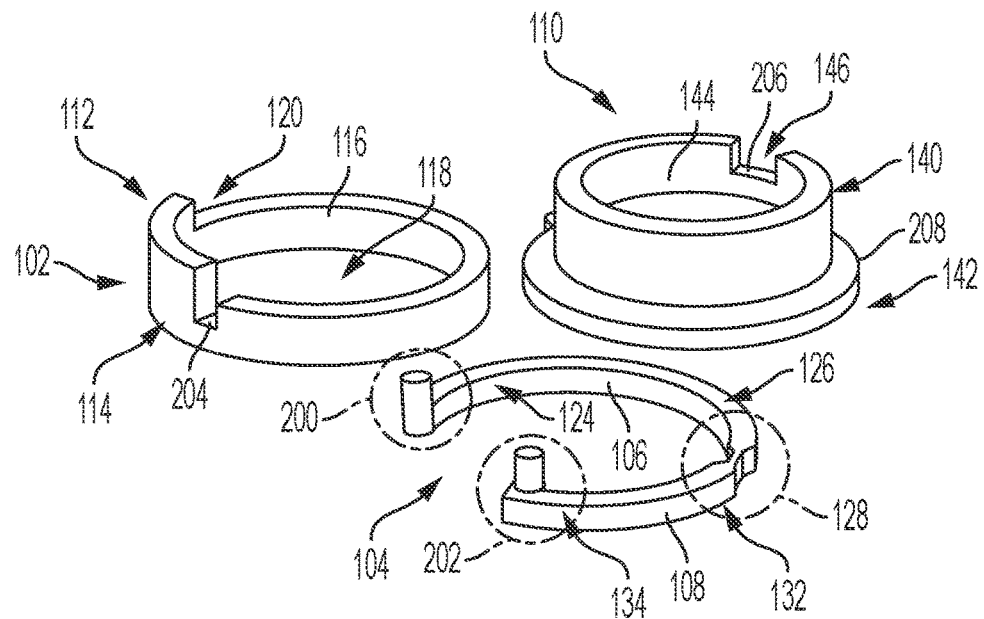
FIG. 8A shows the hollow rod and bi-stable deployment ring components.
Figure 8B:
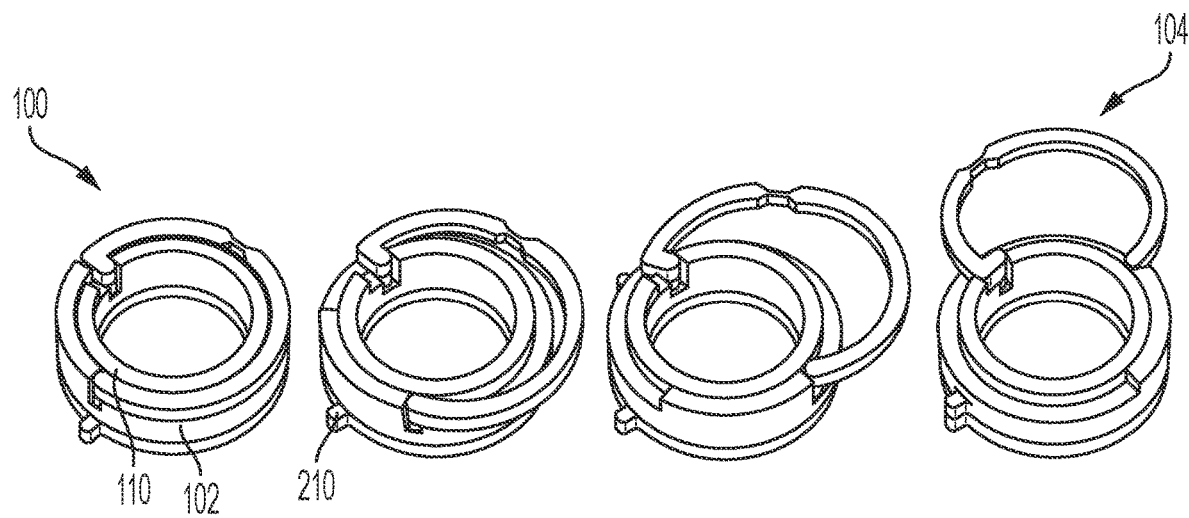
FIG. 8B shows successive illustrations of a hollow rod developable actuator tool with a bi-stable deployment ring actuator mechanism, the tool transitioning through different stages of actuation from stowed within the rod, to partially deployed, to fully deployed.

By applying principles of compliant mechanisms, the pin joints can be replaced by compliant segments and provide the same motion. FIG. 6 shows a compliant version of the mechanism illustrated in FIG. 1. By adjusting the shapes of the links, two instances of the invention mechanism can occupy the same plane as seen in FIGS. 7A and 7B. These compliant configurations allow for more manufacturing methods such as planar CNC routing and die cutting. FIGS. 8A and 8B illustrate the bi-stable structure of the components and assembled deployment mechanism.

In the example of FIG. 6, the pin joints of first joint 122, second joint 128, and third joint 136 of the tool 100 are replaced with compliant mechanism. The compliant mechanism take advantage of the flexible nature of the materials forming the joint to allow to material to flex replicating the degree of motion provided by the conventional pin joint. By using compliant mechanisms, the second link 106 and third link 108 of the first deployment ring 104 as well as the first joint 122, second joint 128, and third joint 136 can be formed of one piece of material. This allows all the portions of the first deployment ring 104 to exist in the same plane perpendicular to the central passage 118.

In the example of FIG. 7A and FIG. 7B, a change in the shape of the deployment rings 104, 150 combined with compliant mechanisms for the second joint 128 and fifth joint 164 allows the first deployment ring 104 and second deployment ring 150 to exist in the same plane perpendicular to the central passage 118 and operate without interference. In this example the first joint 122 and third joint 136 are pin joints consisting of pins extending from the first end 124 of the second link 106 and the second end 134 of third link 108 that are received in corresponding sockets in the first link 102 and fourth link 110. Similarly, the fourth joint 158 and sixth joint 172 are pin joints consisting of pins extending from the first end 156 of the fifth link 152 and the second end 170 of sixth link 154 that are received in corresponding sockets in the first link 102 and fourth link 110. The second joint 128 of the first deployment ring 104 and the fifth joint 164 of the second deployment ring 150 are compliant mechanisms that also provide and offset. The offset and the compliant nature prevent the first deployment ring 104 and second deployment ring 150 from interfering with other when actuated despite both the first deployment ring 104 and second deployment ring 150 existing in the same plane perpendicular to the central passage 118.

FIG. 7A shows the tool 100 in the first closed or stored state wherein the second link 106 and third link 108 of the first deployment ring 104 and the fifth link 152 and sixth link 154 of the second deployment ring 150, as well the mounts 178, 182, are stowed within the outer circumference of the tool 100. FIG. 7B shows the tool 100 in the second open or deployed state wherein the second link 106 and third link 108 of the first deployment ring 104 and the fifth link 152 and sixth link 154 of the second deployment ring 150, as well the mounts 178, 182 attached to the second link 106 and fifth link 152 respectively, extend outside the outer circumference of the tool 100. The actuation of the tool 100 from the first state, as seen in FIG. 7A, to the second state, as seen in FIG. 7B, is achieved by rotating the inner cylinder of the fourth link 110 in relation to the outer cylinder of the first link 102.

FIG. 8A and FIG. 8B present and embodiment of the tool 100 making use of both pin joints and compliant mechanisms to make a tool 100 having a first deployment ring 104 wherein the components are bi-stable and each component is capable of being formed of as a solid piece. FIG. 8A shows the first link 102, first deployment ring 104 and fourth link 110 disassembled.

The outer cylinder of the first link 102 has a first end 112 having a first aperture, a second end 114 having a second aperture at, and a first wall 116 extending between the first end 112 and second end 114 defining an outer circumference of the hollow rod developable actuator tool 100 and a central passage 118 therethrough from the first end 112 to the second end 114. A first cavity 120 is disposed in the first wall 116 having a socket 204 formed therein.

In the example of FIG. 8A and FIG. 8B, the first wall 116 of the first link 102 is formed of plastic. Other suitable materials will be apparent to one skilled in the art given the benefit of this disclosure. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic.

The first cavity 120 in the first wall 116 comprises a cut-away that is sized and dimensioned to allow the at least a portion of the first deployment ring 104 to reside or otherwise be stowed in the first cavity 120 when the mechanism of the present device is in a closed position. In the example of FIG. 8A and FIG. 8B, the first cavity 120 includes a socket 204 in the first wall 116 for the receiving a pin 200 making up the first joint 122.

The second link 106 makes up the first portion of the first deployment ring 104. The second link 106 has a first end 124 pivotably coupled to the first wall 116 of the first link 102 at the first joint 122, a second end 126 having a second joint 128, and a body 130 extending between first end 124 and second end 126. In the example of FIG. 8A and FIG. 8B, the body 130 of the second link 106 is formed of plastic. The body 130 of the second link 106 is curved to conform to the curvature of the first link 102 such that the body 130 of the second link 106 can reside within the first cavity 120 of the first wall 116 when the tool 100 is in a closed state. In this example, a formed pin 200 is provided at the first end 124 of the body 130 to mate with the socket 204 on the first link 102 to make up the first joint 122. The second joint 128 comprises a compliant mechanism, formed by thinning the material at the second joint 128, linking the second link 106 to the third link 108.

The third link 108 makes up the second portion of the first deployment ring 104. The third link 108 has a first end 132 pivotably coupled to the body 130 of the second link 106 via the compliant mechanism of the second joint 128, a second end 134 having a formed pin 202, and a body 138 extending between first end 132 and second end 134. In the example of FIG. 8A and FIG. 8B, the body 138 of the third link 108 is formed of plastic. The body 138 of the third link 108 is curved to conform to the curvature of the first link 102 such that the body 138 of the third link 108 can reside within the first cavity 120 of the first wall 116 when the mechanism is in a closed state. In this example, the formed pin 202 is provided at the second end 134 of the body 130 to mate with a socket 206 on the fourth link 110 to make up the third joint 136.

The first deployment ring 104 made up of the second link 106, third link 108 and second joint 128 linking the second link 106 and third link 108 are formed of plastic. Other suitable materials will be apparent to one skilled in the art given the benefit of this disclosure. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic.

The inner cylinder of the fourth link 110 has a first end 140 having a first aperture, a second end 142 having a second aperture, and a second wall 144 extending between the first end 140 and the second end 142 defining an inner circumference of the hollow rod and the central passage 118 therethrough from the first end 140 to the second end 142. A second cavity 146 is disposed in the second wall 144 having a socket 206 formed therein.

In the example of FIG. 8A and FIG. 8B, the second wall 144 of the fourth link 110 is formed of plastic. Other suitable materials will be apparent to one skilled in the art given the benefit of this disclosure. Examples of suitable materials include stainless steel, titanium, nitinol, tungsten carbide, carbon steels, aluminum, high density polyethylene (HDPE), polypropylene, polylactic acid (PLA), acrylonitrile butadiene styrene (ABS) plastic, polyethylene terephthalate (PET), and acrylic. In this example, the fourth link 110 further includes a lip 208 extending from the first end 140 of the fourth link. The lip 208 can also serve as a support or retention feature for the outer cylinder of the first link 102 when place over the inner cylinder of the fourth link 110. In certain embodiments, the lip 208 may further include a tab 210 for aiding in actuating the tool 100.

The second cavity 146 in the second wall 144 comprises a cut-away that is sized and dimensioned to allow at least a portion of the first deployment ring 104 to reside or otherwise be stowed in the second cavity 146 when the tool 100 is in a closed position. In the example of FIG. 8A and FIG. 8B, the second cavity 146 includes a socket 206 for the receiving a pin 202 making up the third joint 136.

FIG. 8B shows successive images of the assembled tool 100 in operation. The left-most image shows the tool 100 in a first closed or stowed state. The right-most image shows the tool 100 in a second open or deployed state. The actuation of the tool 100 from the first state to the second state is achieved by rotating the inner cylinder of the fourth link 110 in relation to the outer cylinder of the first link 102. In certain embodiments, where a lip 208 and/or tab 210 are provided, the tab 210 and or lip 208 can be used in actuating the tool 100.

Figure 8C:
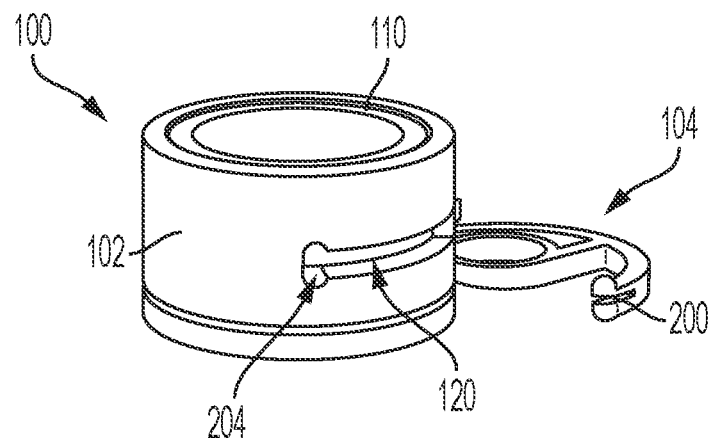
FIG. 8C shows a hollow rod developable actuator tool having a detachable deployment ring with the deployment ring detached.
Figure 8D:
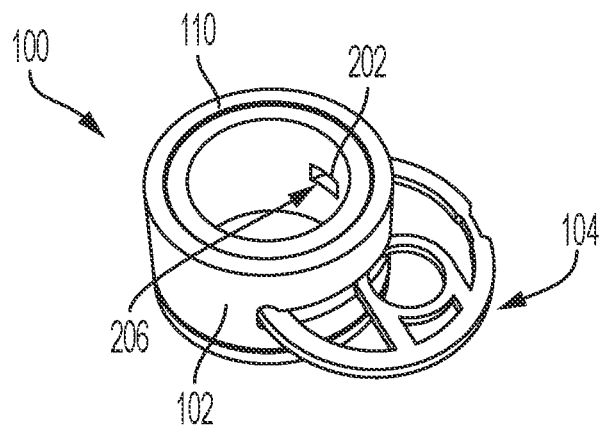
FIG. 8D shows the hollow rod developable actuator tool of FIG. 8C with the deployment ring attached.

FIG. 8C and FIG. 8D present an embodiment of the tool 100 making use of compliant mechanism for the joints connecting the deployment ring 104 to first link 102 and fourth link 110 allowing the deployment ring 104 to be easily attached or detached from the tool 100. FIG. 8C showed the deployment ring 104 detached from the tool 100 while FIG. 8D shows the deployment ring 104 detached from the tool 100. In this embodiment, the formed pin 200 provided for mating with a socket 204 to make up the first joint 122 and the formed pin 202 provided for mating with socket 206 to make up the third joint 136 are compliant mechanisms. Here the compliant mechanism of the formed pins 200, 202 provides a spring-clip mechanism that can the clipped or snapped into the corresponding sockets 204, 206. By using compliant mechanism for the formed pins 200, 202 the deployment ring 104 can be easily attached and detached from the tool 100. This allows for quick configuration of the tool 100 for a specific application by attaching a deployment ring 104 with the desired device 180 or mount for device 178 attached therein. The tool can be reconfigured as desired by detaching the deployment ring 104 and exchanging the deployment ring 104 with another equipped with the desired device 180. Other configurations and suitable compliant mechanism will be apparent to one skilled in the art given the benefit of this disclosure.

Figure 9:
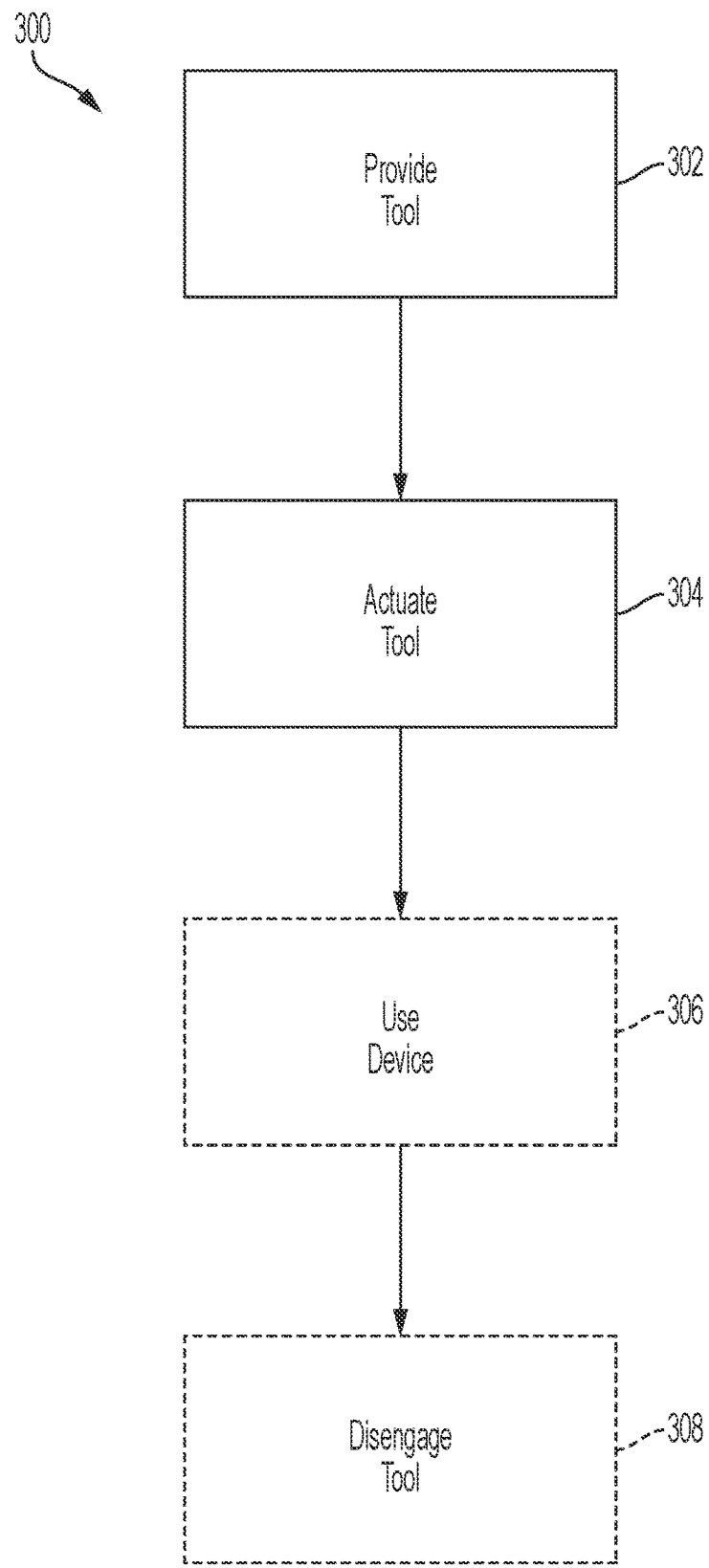
FIG. 9 is a flow diagram depicting a method of using the hollow rod developable actuator tool of the present invention.

FIG. 9 depicts a methodology 300 for using the hollow rod developable actuator tools 100 of the present invention. First a hollow rod developable actuator tool 100 as described herein is provided (Step 302). The tool 100 can be deployed in the particular workspace where hollow rod actuator tools are typically used such as drill site or surgical environment. The tool 100 can then be actuated in the workspace (Step 304) to transition from a first closed or stowed state to a second open or deployed state. In embodiments, wherein the one or more deployment rings 104, 150 of the tool 100 have devices mounted therein, the devices can be use (Step 306). In certain embodiments, the tool 100 may also be transitioned from the second open state back to the first closed state to disengage the tool 100 (Step 308) wherein the tool 100 can be withdrawn from the workspace.

The actuating of the tool 100 (Step 304) is shown in the successive images of FIG. 1, FIG. 4, and FIG. 8B moving left to right with the left-most image being the tool 100, in a first stowed state and the right most image being the tool 100 in a deployed second state wherein the one or more deployment rings 104, 150 extend outside the circumference of the tool 100.

Typically, the first end of the tool 100 would be proximate to a user while the distant second end of the tool 100 where one or more deployment rings 104, 150 are located would be inserted into the workspace. In some embodiments, one or more devices 180, 184 can be attached to the deployment rings 104, 150. It should be understood that the deployment rings 104, 150 can be located anywhere along the length of the tool 100 nor does the second deployment ring 150 have to be in the same general location as the first deployment ring 104.

The actuation of the tool 100 (step 304) from the first state to the second state is achieved by rotating the inner cylinder of the fourth link 110 in relation to the outer cylinder of the first link 102. In certain embodiments, where a lip 208 and/or tab 210 are provided, the tab 210 and or lip 208 can be used in actuating the tool 100.

Once the one or more deployment rings 104, 150 have been extended, if there are devices 180, 184 mounted on the deployment rings 104, 150 the devices can be utilized in the environment outside the outer circumference of the tool 100 (Step 306). Also, once deployed items can be inserted into the environment through the central passage 118 of the tool. An example of this can be seen in FIG. 10.

Figure 10:
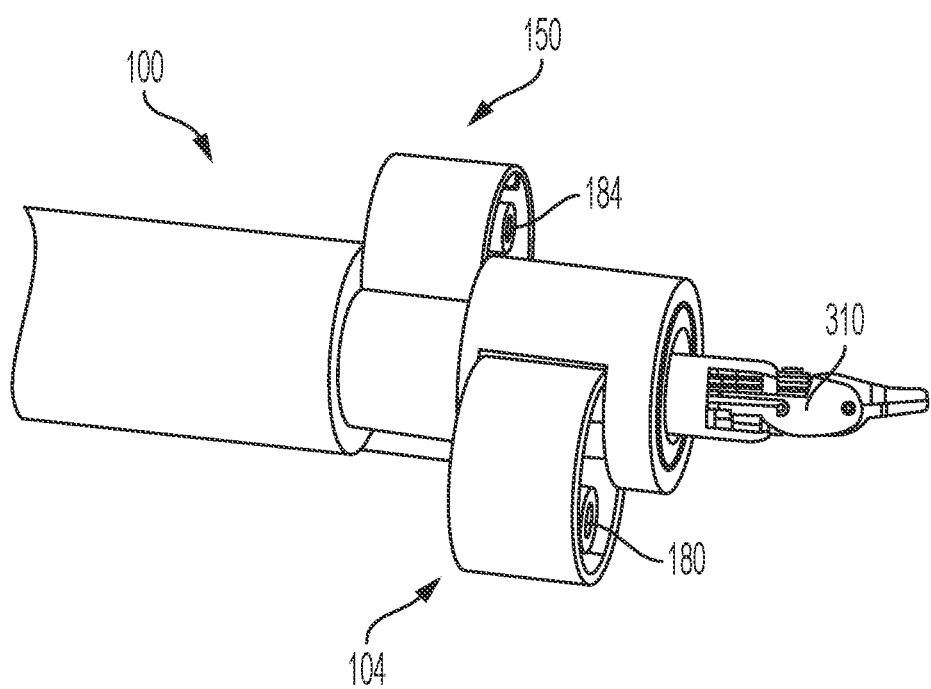
FIG. 10 depicts a hollow rod developable actuator tool with deployment rings extended and an object inserted through the central passage.

In FIG. 10 a second end of the tool 100 is shown with the first deployment ring 104 and second deployment ring 150 deployed outside the circumference of the tool 100. In this example the first device 180 attached to the first deployment ring 104 is a camera with built-in light source. The second device 184 attached to the second deployment ring is also a camera with built-in light source.

In the example, of FIG. 10, with the deployment rings 104, 150 extended, the central passage 118 of the tool 100 is available to be used for the insertion of additional items into the environment of the workspace. In this example, forceps 310 have been inserted through the central passage 118 of the tool 100. In use, the cameras 180, 184 provided on the deployment rings 104, 150 provide a stereoscopic view of the environment allowing the user to see what is being interacted with using the forceps 310. In certain other embodiments, one of the cameras 180, 184 can be mounted facing the opposite direction giving the user a different view of the environment. This provides an advantage over traditional endoscopes that need to be repositioned to obtain a different view.

Returning now to FIG. 9, in a similar manner, the tool 100 can be disengaged (step 308), by transitioning the tool 100 from the deployed second state to the first stowed state. Transitioning the tool from the second open or deployed state to the first closed or stowed state involves rotating the inner cylinder of the fourth link 110 in relation to the outer cylinder of the first link 102 in the opposite direction of rotation than was used to transition the tool 100 from the first closed or stowed state tot the second open or deployed state. At such time, the tool 100 can be withdrawn from the environment.

It is stressed that the shape of the links is arbitrary for mechanism motion. As long as the distance between the pins remains the same and the links do not self-interfere, the mechanism will have the same motion. To completely conceal the moving links when the mechanism is closed, the links are constrained to a radius of curvature of the actuating cylinders and to a shape that will fit inside the cylinders when fully collapsed.

Conventional cylindrical shaft or tube tools often allow only one tool to operate at the end of the shaft, especially when the tubes are small. The present invention enables an instrument or mechanism to be included in the cylindrical tube and to enter a workspace through a single entrance in combination with other instruments concealed on the shaft. This can i) lower the time required to perform a task in a confined/remote workspace by reducing the number of tooling changes required; ii) reduce the trauma/damage to the boundary of the workspace by reducing the number of entrance holes/points required; iii) reduce trauma/damage to the workspace by limiting interface between the blades/grippers and body tissue, since the only tissue interacting with the blades/grippers is that which is drawn into the inner diameter of the cylindrical shaft; iv) reduce the complexity of the control system used in conjunction with the tooling setup, as fewer shafts would be required to enter the space, v) reduce the number of devices that need to be inserted/deployed as devices are incorporated into tool, vi) reduce complexity involved in repositioning as devices attached to tool move with tool when tool is repositioned, viii) reduce the cost of the procedure; ix) reduce the number of working hands required to stabilize or operate individual tools, and x) increase capabilities when working in confined spaces by providing a multitude of tools/equipment needed to complete an operation such as light, camera, and tool when previously there was only space for a single tool.

In accordance with example embodiments of the present invention, the deployment device can be utilized in places where cylindrical shafts are in tight spaces and they could benefit from additional functionality. Two critical applications include minimally invasive surgery instruments and down-hole drilling equipment. Other applications include electronics with cylindrical shafts such as a laser, flashlight, camera lens, motor, speaker, charging port, and so on.

A charging device can have its connection elements hidden until they are needed then expand out to charge or be charged. Controls on a speaker (e.g. Amazon Alexa) can keep buttons and ports hidden for appearance and protected from contamination.

When changing a battery or trying to repair wiring inside a device, having the "insides" expand out enables an easy way to repair or change the battery, then push back into the cylinder.

On a camera lens, there are multiple glass disks that determine how the lens functions. If those disks could be simply added or removed in different spots along the lens, it would essentially become a single universal lens rather than a large collection of independent lenses. This could apply to anything for which it may be desirable to adjust the focal point. This could be particularly useful for the mobile camera revolution.

There are hundreds of lens filters that attach to the end of lenses, e.g. color filters, UV filters, etc. If all these filters were attached along the lens and to be simply slid in and out, it would be extremely convenient and easy to carry/change filters.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A hollow rod developable actuator tool, the tool comprising:
   a first link comprising an outer cylinder, the outer cylinder comprising: a first end having a first aperture;
      a second end having a second aperture,
      a first wall extending between the first end and second end defining an outer circumference of the hollow rod and a central passage therethrough from the first end to the second end; and
      a first cavity disposed in the first wall having a first joint mounted therein;
   a deployment ring comprising:
      a second link comprising a first portion of the deployment ring, the first portion comprising:
         a first end pivotably coupled to the first wall of the first link at the first joint;
         a second end having a second joint; and
         a body extending between first end and second end; and
      a third link comprising a second portion of the deployment ring, the second portion comprising:
         a first end pivotably coupled to the body of the second link at the second joint;
         a second end pivotably connected to a third joint; and
         a body extending between the first end and second end; and
   a fourth link comprising an inner cylinder disposed within the central passage of the outer cylinder of the first link, the inner cylinder comprising:
      a first end having a first aperture;
      a second end having a second aperture;
      a second wall extending between the first end and the second end defining an inner circumference of the hollow rod and a central passage therethrough from the first end to the second end; and
a second cavity in the second wall having the third joint pivotably coupled to the body of the third link;
wherein, when the inner cylinder of the fourth link is rotated in relation to the outer cylinder of the first link in such a way that moves the first joint and third joint away from each other along the perimeter of the tool, the tool transitions from a first state wherein the deployment ring is within the first cavity and the second cavity of the respective first wall and second wall to a second state where the deployment ring extends outside the outer circumference of the tool.

2. The hollow rod developable actuator tool of claim 1, wherein a device is attached to the deployment ring.

3. The hollow rod developable actuator tool of claim 2, wherein a mount is provided for attaching the device to the deployment ring.

4. The hollow rod developable actuator tool of claim 1, wherein at least one of the body of the second link and the body of the third link are curved to match the curvature of the first link making the second link and third link flush with the outer circumference when the actuator tool is in the first state.

5. The hollow rod developable actuator tool of claim 1, wherein the first cavity and the second cavity are located in proximity to the second end of the first link and the second end of the fourth link.

6. The hollow rod developable actuator tool of claim 1, wherein the second joint connecting the second link and third link of the deployment ring is a compliant segment.

7. The hollow rod developable actuator tool of claim 1, wherein the first joint and third joint are compliant segments.

8. The hollow rod developable actuator tool of claim 1 further comprising a second deployment ring, the second deployment ring comprising:
a fifth link comprising a first portion of the second deployment ring, the first portion comprising:
a first end pivotably coupled to the first wall of the first link at a fourth joint in a third cavity in the first link;
a second end having a fifth joint;
a body extending between first end and second end;
a sixth link comprising a second portion of the deployment ring, the second portion comprising:
a first end pivotably coupled to the body of the fifth link at the fifth joint;
a second end pivotably connected to the second wall of the fourth link at a sixth joint in a fourth cavity in the fourth link; and
a body extending between the first end and second end;
wherein, when the inner cylinder of the fourth link is rotated in relation to the outer cylinder of the first link in such a way that moves the fourth joint and sixth joint away from each other along the perimeter of the hollow rod, the actuator tool transitions from a first state wherein the second deployment ring is within the first cavity and the second cavity of the respective first wall and second wall to a second state where the second deployment ring extends outside the outer circumference of the hollow rod.

9. The hollow rod developable actuator tool of claim 8, wherein a device is attached to the second deployment ring.

10. The hollow rod developable actuator tool of claim 9, wherein a mount is provided for attaching the device to the second deployment ring.

11. The hollow rod developable actuator tool of claim 8, wherein at least one of the body of the fifth link and the body of the sixth link are curved to match the curvature of the first link making the fifth link and sixth link flush with the outer circumference when the actuator tool is in the first state.

12. The hollow rod developable actuator tool of claim 8, wherein the fifth joint connecting the fifth link and sixth link of the second deployment ring is a compliant segment.

13. The hollow rod developable actuator tool of claim 8, wherein the fourth joint and sixth joint are compliant segments.

14. A method of using a hollow rod developable actuator tool, the method comprising: Providing a hollow rod developable actuator tool, the tool comprising:
a first link comprising an outer cylinder, the outer cylinder comprising: a first end having a first aperture;
a second end having a second aperture,
a first wall extending between the first end and second end defining an outer circumference of the hollow rod and a central passage therethrough from the first end to the second end; and
a first cavity disposed in the first wall having a first joint mounted therein;
a deployment ring comprising:
a second link comprising a first portion of the deployment ring, the first portion comprising:
a first end pivotably coupled to the first wall of the first link at the first joint;
a second end having a second joint; and
a body extending between first end and second end;
a third link comprising a second portion of the deployment ring, the second portion comprising:
a first end pivotably coupled to the body of the second link at the second joint;
a second end pivotably connected to a third joint; and
a body extending between the first end and second end;
a fourth link comprising an inner cylinder disposed within the central passage of the outer cylinder of the first link, the inner cylinder comprising:
a first end having a first aperture;
a second end having a second aperture;
a second wall extending between the first end and the second end defining an inner circumference of the hollow rod and a central passage therethrough from the first end to the second end; and
a second cavity in the second wall having the third joint pivotably coupled to the body of the third link;
wherein, when the inner cylinder of the fourth link is rotated in relation to the outer cylinder of the first link in such a way that moves the first joint and third joint away from each other along the perimeter of the tool, the actuator tool transitions from a first state wherein the deployment ring is within the first cavity and the second cavity of the respective first wall and second wall to a second state where the deployment ring extends outside the outer circumference of the tool; and
actuating the tool by rotating the inner cylinder of the fourth link in relation to the outer cylinder of the first link in such a way that moves the first joint and third joint away from each other along the perimeter of the tool to transition the tool from a first state to the second state.

15. The method of claim 14, further comprising:
rotating the inner cylinder of the fourth link in relation to the outer cylinder of the first link in such a way that moves the first joint and third joint toward each other along the perimeter of the tool to transition the tool from a second state to the first state.

\* \* \* \* \*